(12) United States Patent
Durlach et al.

(10) Patent No.: US 11,468,986 B2
(45) Date of Patent: *Oct. 11, 2022

(54) TECHNIQUES FOR REMOTELY CONTROLLING A MEDICAL DEVICE BASED ON IMAGE DATA

(71) Applicant: Stryker Corporation, Kalamazoo, MI (US)

(72) Inventors: Thomas Durlach, Kalamazoo, MI (US); Ross Nave, Kalamazoo, MI (US); Krishna Sandeep Bhimavarapu, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/236,385

(22) Filed: Apr. 21, 2021

(65) Prior Publication Data

US 2021/0241904 A1 Aug. 5, 2021

Related U.S. Application Data

(63) Continuation of application No. 16/864,354, filed on May 1, 2020, now Pat. No. 11,011,272, which is a (Continued)

(51) Int. Cl.
*G16H 40/67* (2018.01)
*A61B 5/00* (2006.01)
(Continued)

(52) U.S. Cl.
CPC ............ *G16H 40/67* (2018.01); *A61B 5/002* (2013.01); *A61B 5/0013* (2013.01);
(Continued)

(58) Field of Classification Search
CPC ........ G16H 40/67; G16H 40/20; G16H 80/00; A61B 5/0013; A61B 5/002; A61B 5/0024;
(Continued)

(56) References Cited

U.S. PATENT DOCUMENTS 7,109,848 B2 9/2006 Schybergson
7,319,386 B2 1/2008 Collins, Jr. et al.
(Continued)

*Primary Examiner* — Daniell L Negron
(74) *Attorney, Agent, or Firm* — Howard & Howard Attorneys PLLC

(57) ABSTRACT

A system and a method for remotely controlling a medical device based on image data are disclosed. The system includes a medical device, an image sensor, and a remote caregiver interface. The medical device includes a controller coupled to a communication network. The image sensor is coupled to the communication network and is configured to capture image data. The remote caregiver interface is coupled to the communication network and is configured to display the image data for viewing by a user, receive a selected remote control function from the user, and transmit an input signal corresponding to the selected remote control function to the controller of the medical device to execute the selected remote control function based on the input signal.

19 Claims, 11 Drawing Sheets

Related U.S. Application Data continuation of application No. 16/211,929, filed on Dec. 6, 2018, now Pat. No. 10,679,748.

(60) Provisional application No. 62/609,809, filed on Dec. 22, 2017.

(51) Int. Cl.
*G16H 40/20* (2018.01)
*G16H 80/00* (2018.01)

(52) U.S. Cl.
CPC .......... *A61B 5/0024* (2013.01); *A61B 5/0077* (2013.01); *A61B 5/6892* (2013.01); *A61B 5/7435* (2013.01); *G16H 40/20* (2018.01); *G16H 80/00* (2018.01)

(58) Field of Classification Search
CPC .... A61B 5/0077; A61B 5/6892; A61B 5/7435
See application file for complete search history.

(56) References Cited

U.S. PATENT DOCUMENTS

| | | |
|---|---|---|
| 7,557,689 B2 | 7/2009 | Seddigh et al. |
| 7,808,391 B2 | 10/2010 | Nixon |
| 7,958,201 B2 | 6/2011 | Lindsay |
| 8,856,383 B2 | 10/2014 | Beninato et al. |
| 9,094,723 B2 | 7/2015 | Reams |
| 9,185,202 B2 | 11/2015 | Herbst et al. |
| 9,204,823 B2 | 12/2015 | Derenne et al. |
| 9,305,450 B2 | 4/2016 | Halverson et al. |
| 9,307,033 B1 | 4/2016 | Meschkat |
| 9,513,899 B2 | 12/2016 | Collins, Jr. et al. |
| 9,833,194 B2 | 12/2017 | Hayes et al. |
| 10,679,748 B2 * | 6/2020 | Durlach ................ G16H 80/00 |
| 11,011,272 B2 * | 5/2021 | Durlach ............... A61B 5/6892 |
| 11,074,802 B2 | 7/2021 | Wong et al. |
| 2002/0014951 A1 | 2/2002 | Kramer et al. |
| 2007/0174964 A1 | 8/2007 | Lemire et al. |
| 2008/0082211 A1 | 4/2008 | Wang et al. |
| 2014/0000609 A1 | 1/2014 | Steinhauer et al. |
| 2014/0259414 A1 | 9/2014 | Hayes et al. |
| 2014/0297327 A1 | 10/2014 | Heil et al. |
| 2015/0281659 A1 | 10/2015 | Hood et al. |
| 2016/0199240 A1 | 7/2016 | Newkirk et al. |
| 2016/0259906 A1 | 9/2016 | Iucha et al. |
| 2016/0367420 A1 | 12/2016 | Zerhusen et al. |
| 2020/0258626 A1 | 8/2020 | Durlach et al. |

* cited by examiner

TECHNIQUES FOR REMOTELY CONTROLLING A MEDICAL DEVICE BASED ON IMAGE DATA

CROSS-REFERENCE TO RELATED APPLICATIONS

The subject patent application is a Continuation of U.S. patent application Ser. No. 16/864,354, filed on May 1, 2020, which is a Continuation of U.S. patent application Ser. No. 16/211,929, filed on Dec. 6, 2018, which, in turn, claims priority to all the benefits of U.S. Provisional Patent Application No. 62/609,809 filed on Dec. 22, 2017, the disclosures of each of which are hereby incorporated by reference in their entirety.

BACKGROUND

Remote control functions may be used to control a medical devices from a remote location. Such medical devices may include, for example, patient support apparatuses, such as hospital beds, stretchers, cots, tables, wheelchairs, recliners, and chairs for patient care. Other medical devices may include equipment such as lights, televisions, temperature management systems, respirators, IV lines, surgical tools, and heart rate monitors that may be used in medical procedures or in the provision of medical services to patients. For example, a remote control function may incline a back section of the patient support apparatus, activate a speaker of the patient support apparatus, adjust a height of the patient support apparatus, engage a side rail of the patient support apparatus, and/or provide turning assistance by the patient support apparatus. The remote control functions may be in response to patient requests.

Typically, remote control functions may be initiated by a caregiver who is assigned to the patient or the patient support apparatus, but is not in the same room or near the patient. Therefore, due to the nature of a remote control function, caregivers may not be able to interact with or view their patients prior to or during an execution of a remote control function. The patient's comfort or safety may therefore be inadvertently compromised by the execution of the remote control function. As such, there are opportunities to address at least the aforementioned problems.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Referring to the Figures, wherein like numerals indicate like or corresponding parts throughout the several views, techniques for remotely controlling medical devices based on image data are provided.

A system for remotely controlling a medical device based on image data is disclosed. The system includes a medical device including a controller coupled to a communication network. The system also includes an image sensor coupled to the communication network and being configured to capture image data an area including the medical device. Additionally, the system includes a remote caregiver interface coupled to the communication network. The remote caregiver interface is configured to display the image data, receive a selected remote control function from the user, and transmit an input signal to the controller of the medical device to execute the selected remote control function.

The system may remotely control a variety of medical devices based on image data. For example, in one embodiment, the system may remotely control a temperature management device, such as a blanket warming device, based on image data. In such an embodiment, the blanket warming device may be configured to warm a blanket placed on a patient based on image data. For example, the system may remotely control the blanket warming device to warm the blanket based on a temperature of the patient, a temperature of a hospital room, or a temperature of a patient support apparatus of a hospital room, which may be determined based on infrared image data.

In another embodiment, the system may remotely control an intravenous therapy device based on a condition of the patient, which may be determined based on image data of the patient. For example, in one embodiment, the system may control the intravenous therapy device to deliver fluids or medications to the patient based a patient presence, a comfort indication of the patient, or a physiological state of the patient. In one such embodiment, the intravenous therapy device may be configured to deliver fluids to a patient with a fever.

In other embodiments, the system may remotely control other medical devices based on image data. For instance, the system may remotely control medical devices such as, but not limited to, a heart rate monitor, a medical ventilator device, a light in a hospital room, a television in a hospital room, or any other such medical device.

Figure 1:
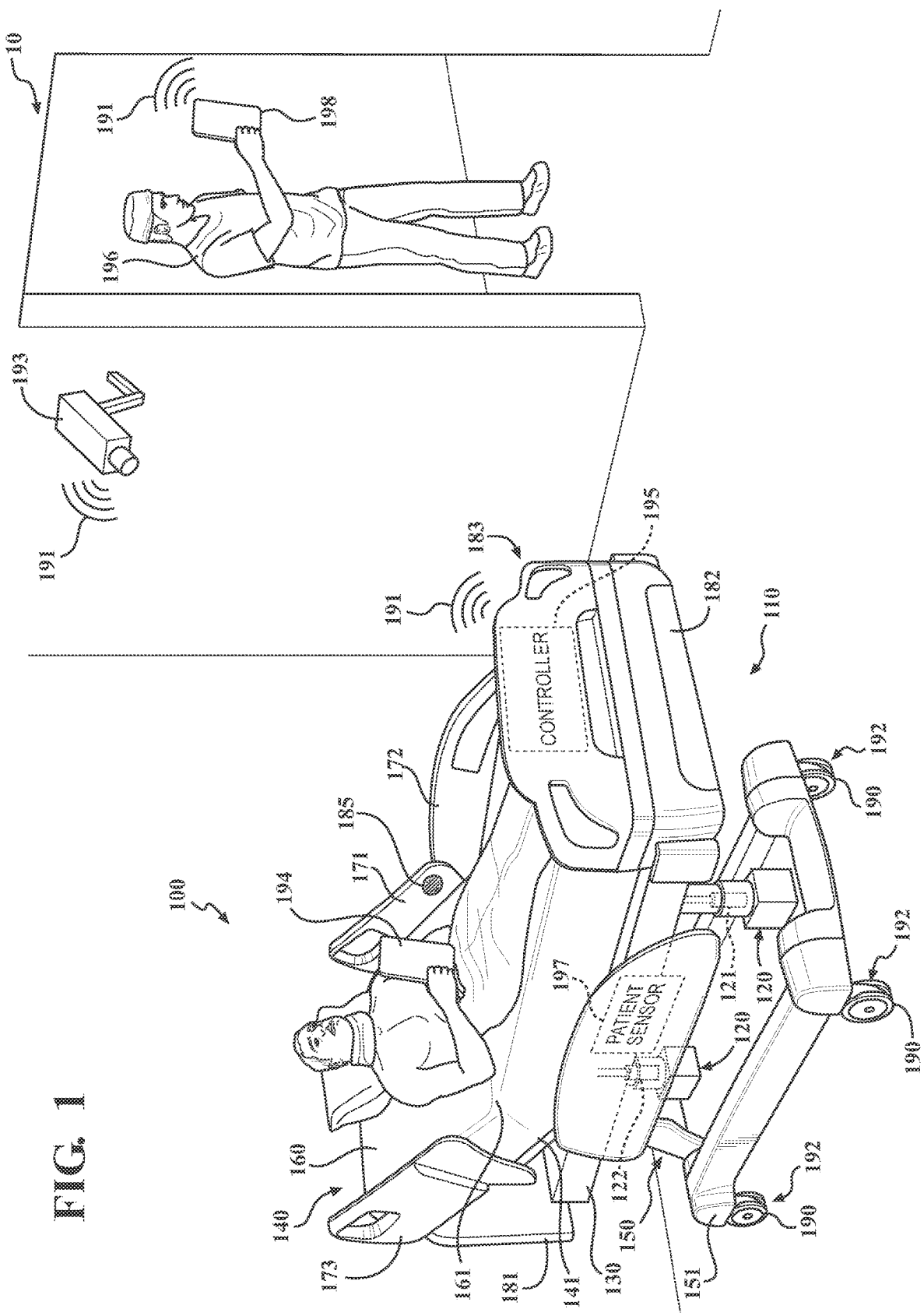
FIG. 1 is a perspective view of a system including a patient support apparatus, a controller, a remote caregiver interface, and an image sensor.

In the embodiment of FIG. 1, the medical device is a patient support apparatus 100 for supporting a patient in a health care setting. The patient support apparatus 100 illustrated in FIG. 1 includes a hospital bed. However, in other embodiments, the patient support apparatus 100 may include a stretcher, a cot, a table, a wheelchair, a recliner, a chair for patient care, or any other similar apparatus utilized in the care of a patient.

A support structure 110 provides support for the patient. The support structure 110 illustrated in FIG. 1 includes a base 150 and a support frame 130. The base 150 includes a base frame 151. The support frame 130 is spaced above the base frame 151 in FIG. 1. The support structure 110 also includes a patient support deck 140 disposed on the support frame 130. The patient support deck 140 includes several sections, some of which are capable of articulating relative to the support frame 130, such as a back section, a seat section, a thigh section, and a foot section. The patient support deck 140 provides a patient support surface 141 upon which the patient is supported.

A mattress 160 may be disposed on the patient support deck 140 during use. The mattress 160 includes a secondary patient support surface 161 upon which the patient is supported. In addition, the mattress 160 may be omitted in certain embodiments, such that the patient rests directly on the patient support surface 141.

The base 150, support frame 130, patient support deck 140, and patient support surface 141 each have a head end and a foot end corresponding to a designated placement of the patient's head and feet on the patient support apparatus 100. The construction of the support structure 110 may take on any suitable design, and is not limited to that specifically set forth above.

Side rails 171, 172, 173, 174 are coupled to the support frame 130 or the patient support deck 140 and are thereby supported by the base 150. A first side rail 171 is positioned at a left head end of the patient support deck 140. A second side rail 172 is positioned at a left foot end of the support frame 130. A third side rail 173 is positioned at a right head end of the patient support deck 140. A fourth side rail 174 is positioned at a left foot end of the support frame 130. If the patient support apparatus 100 is a stretcher or a cot, there may be fewer side rails. The side rails 171, 172, 173, 174 are movable to a raised position in which they block ingress and egress into and out of the patient support apparatus 100, one or more intermediate positions, and a lowered position in which the side rails 171, 172, 173, 174 are not an obstacle to such ingress and egress. In still other configurations, the patient support apparatus 100 may not include any side rails.

A headboard 181 and a footboard 182 are coupled to the support frame 130. In other embodiments, when the headboard 181 and footboard 182 are included, the headboard 181 and footboard 182 may be coupled to other locations on the patient support apparatus 100, such as the base 150. In still other embodiments, the patient support apparatus 100 does not include the headboard 181 and/or the footboard 182.

Caregiver interfaces 183, such as handles, are shown integrated into the footboard 182 and side rails 171, 172, 173, 174 to facilitate movement of the patient support apparatus 100 over floor surfaces. Additional caregiver interfaces 183 may be integrated into the headboard 181 and/or other components of the patient support apparatus 100. The caregiver interfaces 183 are graspable by a caregiver to manipulate the patient support apparatus 100 for movement.

Wheels 190 are coupled to the base 150 to facilitate transport over the floor surfaces. The wheels 190 are arranged in each of four quadrants of the base 150 adjacent to corners of the base 150. In the embodiment shown, the wheels 190 are caster wheels able to rotate and swivel relative to the support structure 110 during transport. Each of the wheels 190 forms part of a caster assembly 192. Each caster assembly 192 is mounted to the base 150. It should be understood that various configurations of the caster assemblies 192 are contemplated. In addition, in some embodiments, the wheels 190 are not caster wheels and may be non-steerable, steerable, non-powered, powered, or combinations thereof. Additional wheels are also contemplated. For example, the patient support apparatus 100 may include four non-powered, non-steerable wheels, along with one or more powered wheels. In some cases, the patient support apparatus 100 may not include any wheels.

In other embodiments, one or more auxiliary wheels (powered or non-powered), which are movable between stowed positions and deployed positions, may be coupled to the support structure 110. In some cases, when these auxiliary wheels are located between caster assemblies 192 and contact the floor surface in the deployed position, they cause two of the caster assemblies 192 to be lifted off the floor surface thereby shortening a wheel base of the patient support apparatus 100. A fifth wheel may also be arranged substantially in a center of the base 150.

As shown in FIG. 1, the system 10 may include an actuatable device 120 and actuators 121, 122. The actuators 121, 122 may be further defined as being capable of moving the actuatable device 120. The actuators 121, 122 may be coupled to the support structure 110 to move the patient when the patient is disposed on the patient support structure 110. In the embodiment of the patient support apparatus 100 shown in FIG. 1, the patient support apparatus 100 includes two actuators 121, 122. However, it is to be noted that the patient support apparatus 100 may include any suitable number of actuators 121, 122. Furthermore, any of the techniques described herein can utilize any number of actuators 121, 122 individually or in combination.

The actuators 121, 122 should be broadly understood as a type of motor or device that is capable of moving or controlling a mechanism or a system. For example, some suitable, non-limiting examples of the actuators 121, 122 are mechanical, hydraulic, pneumatic, electric, thermal, or magnetic actuators. The actuators 121, 122 may also include motors, such as a rotational or linear motor. In a further example, the actuators 121, 122 may include an inflation actuator. In sum, it should be understood that any type of actuator can be used in certain applications.

As described above, the actuators 121, 122 may be further defined as being capable of moving an actuatable device 120. These actuatable devices 120 are not particularly limited, and may include any device or system that includes one or more actuators 121, 122. In certain embodiments, the actuatable device 120 is one that, when actuated, results in a change of position of the patient support surfaces 141, 161 of the patient support structure 110. This change in position of one or more patient support surfaces 141, 161 when the patient occupies the patient support apparatus 100, results in a change in the position of one or more portions of the patient's body.

More specifically, in situations where a patient occupies the patient support apparatus 100, i.e., contacts one or more patient support surfaces 141, 161, operation of each of the actuatable devices 120 results in movement of one or more portions of the patient in one or more dimensions relative to a static surface, such as relative to a floor of a hospital. Examples of such movement include, but are not limited to: forward and reverse movement of the patient by virtue of movement of the patient support structure 110 along a floor; raising and lowering movement of the patient by virtue of movement of the patient support structure 110 upward and downward relative to the floor; angular movement by virtue of changing the angle of at least a portion of the patient support structure 110 relative to a floor; rotation of the patient along a longitudinal axis of the patient support structure 110 (while the patient support apparatus 100 remains stationary relative to the floor); or various combinations of those types of movement.

Without limitation, the actuatable devices 120 that result in the change of the position of one or more patient support surfaces 141, 161 of the patient support structure 110 may include a coordinated motion device, a patient raising device, a patient turning device, a patient centering device, a patient ingress/egress device, a lift device, a fowler adjustment device, a gatch adjustment device, a side rail engagement device, and a transport device.

It is also contemplated that the actuatable device 120 may be of the type that does not result in a change of position, orientation, and/or elevation of the patient support surfaces 141, 161. These "non-position actuatable devices" may include, but are not limited to, a patient comfort device, such as an entertainment device, a lighting device, a temperature device, a humidity device, and an aromatherapy device, as well as patient therapy devices, such as vibration therapy devices, percussion therapy devices, compression therapy devices, patient warming devices, and electrical stimulation devices. The rate of operation of these non-position actuatable devices can also be controlled by changing the frequency, tempo, rate of temperature change, rate of humidity change, intensity of therapy, etc. of the devices.

The patient support apparatus 100, as shown in FIG. 1, also includes a controller 195. In FIG. 1, the controller 195 is illustrated as being disposed within the footboard 182. However, in other embodiments, the controller 195 may be disposed on or within the headboard 181, the side rails 171, 172, 173, 174, the caregiver interfaces 183, or any other suitable component of the patient support apparatus 100.

The system 10 may also include an image sensor 193 for capturing image data of an area including the patient support apparatus 100, referred to herein as the "patient support apparatus image data". In the embodiment shown in FIG. 1, the image sensor 193 may be included as part of a surveillance camera. However, in other embodiments, the image sensor may be included as part of any device suitable for capturing the patient support apparatus image data, such as a digital camera, a thermographic camera, a webcam, a video camera, a livestream broadcast camera, an infrared image sensor, or combinations thereof. Accordingly, the patient support apparatus image data may vary according to the image sensor 193. For example, if the image sensor 193 is a digital camera, the patient support apparatus image data may be a photo. In another example, if the image sensor 193 is a video camera, the patient support apparatus image data may be a video. In yet another example, if the image sensor 193 is a thermographic camera, the patient support apparatus image data may be thermal image data.

Furthermore, as shown in FIG. 1, the image sensor 193 is coupled to a wall of the hospital room. In other embodiments, the image sensor 193 may be located in any location on a medical device or in any location suitable for capturing the patient support apparatus image data. For example, in other embodiments, the image sensor 193 may be mounted to a ceiling of the hospital room, a floor of the hospital room, or a support structure of the hospital room. In other embodiments, the image sensor 193 may be coupled to the patient support apparatus 100. For example, the image sensor 193 may be disposed on or within the headboard 181, the footboard 182, any of the side rails 171, 172, 173, 174, the caregiver interfaces 183, or any other suitable component of the patient support apparatus 100.

The system 10 may also include a remote caregiver interface 198 for use by a caregiver 196. In the embodiment shown in FIG. 1, the remote caregiver interface 198 is a tablet device. However, the remote caregiver interface 198 may be any suitable remote computing device. For example, the remote caregiver interface 198 may be any one of a desktop computer or a nurse call station. In other embodiments, the remote caregiver interface may be any suitable mobile computing device such as a cellular phone, a laptop, or a wearable remote device.

In some embodiments, the remote caregiver interface 198 may include a camera for capturing image data, referred to herein as the "caregiver image data". For example, the caregiver image data may be of the caregiver 196 or a face of the caregiver 196. Furthermore, the camera for capturing the caregiver image data may be any suitable camera, such as a digital camera, a thermographic camera, a webcam, a video camera, a livestream broadcast camera, or any other device suitable for capturing the caregiver image data. Additionally, the camera for capturing the caregiver image data may be disposed on or within the remote caregiver interface 198. Such features may allow the patient to see the face of the caregiver who is controlling their patient support apparatus 100.

In some embodiments, the remote caregiver interface 198 may include a microphone for capturing audio data, referred to herein as the "caregiver audio data". For example, the caregiver audio data may be a voice of the caregiver 196. Furthermore, the microphone for capturing the caregiver audio data may be any suitable microphone, such as a condenser microphone, a dynamic microphone, a piezoelectric microphone, an electret microphone, a wireless microphone, or a wearable microphone. Additionally, the microphone for capturing the caregiver audio data may be disposed on or within the remote caregiver interface 198. Such features may allow the patient to hear the voice of the caregiver 196 who is controlling their patient support apparatus 100.

Figure 9:
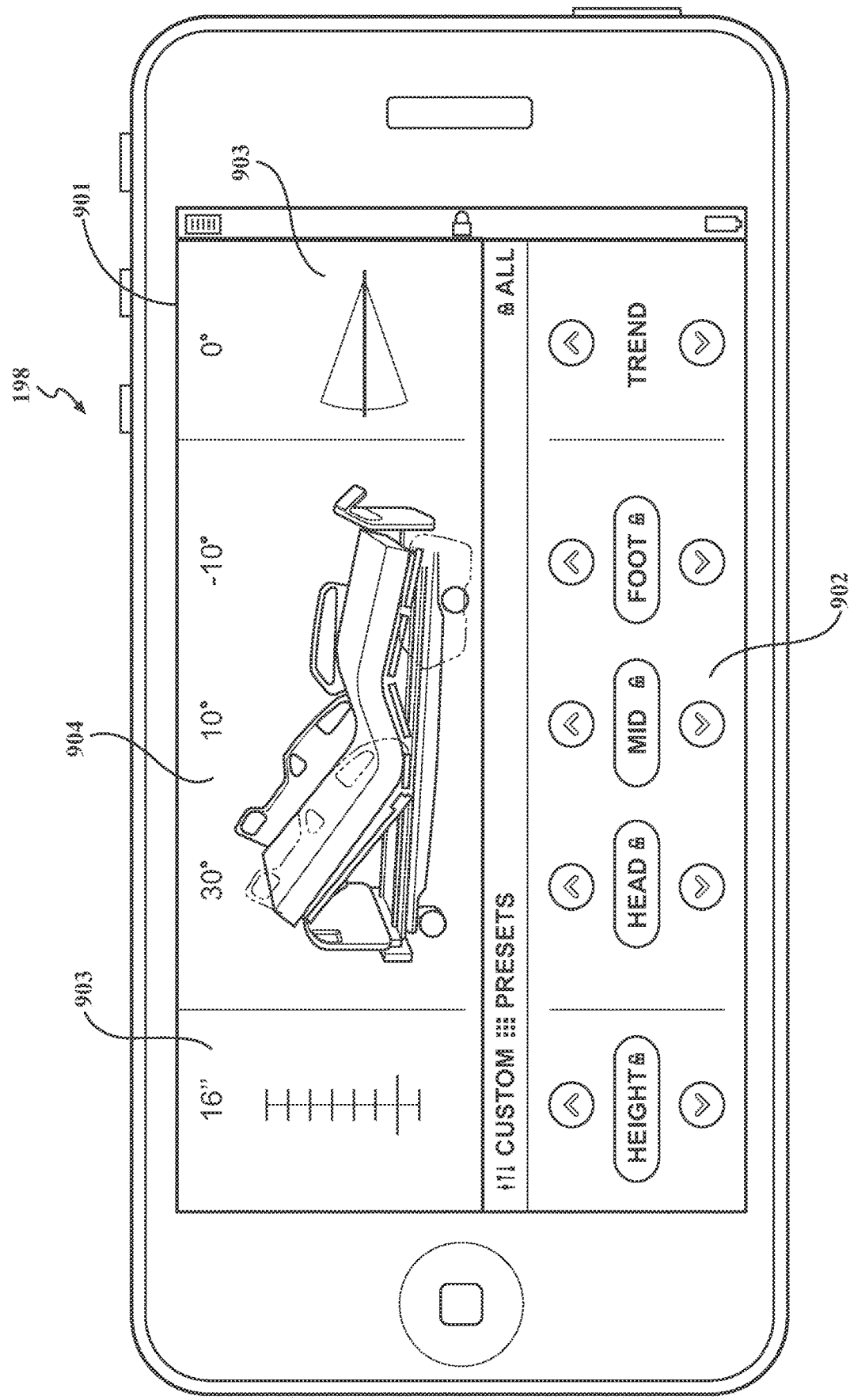
FIG. 9 is a view of an embodiment of the remote caregiver interface.

The remote caregiver interface 198 may be configured to display a graphical user interface. One example of the remote caregiver interface 198 and the graphical user interface is illustrated in FIG. 9.

It should be noted that, while the embodiment shown in FIG. 1 includes one remote caregiver interface 198, the system 10 may include any suitable number of remote caregiver interfaces 198. For example, in some embodiments, the system 10 may also include a second remote caregiver interface for use by a second caregiver and a third remote caregiver interface for use by a third caregiver.

Furthermore, the system 10 may be designed to be used by any suitable number or types of caregivers 196. For example, the system 10 may be used by a first caregiver, who may be the caregiver initially assigned to the patient or the patient's primary caregiver. In some embodiments, the system 10 may also designate a second caregiver as a backup caregiver to the first caregiver. In other embodiments, the second caregiver may be chosen from a group of available caregivers. The system 10 may also appoint a master caregiver, who may be assigned to monitor multiple patients. For example, the third caregiver may be a nurse who is assigned to the nurse call station or who is assigned to monitor multiple patients at a local or remote command center. Of course, the system 10 may be designed for use by more than two caregivers, and may include any suitable number of remote caregiver interfaces 198.

The system 10 may also include a local user interface 194. In some embodiments, the local user interface 194 may be disposed on the patient support apparatus 100. For example, the local user interface 194 may be a user interface of the patient support apparatus 100 such as a touchscreen of the patient support apparatus 100, buttons of the patient support apparatus 100, or switches of the patient support apparatus 100.

In other embodiments, the local user interface 194 may be separated from the patient support apparatus 100. For example, the local user interface 194 may be mounted to a ceiling of a hospital room, a support structure of the hospital room, or a wall of the hospital room. In another example, the local user interface 194 may be a mobile computing device. For example, the local user interface 194 may be any one of a cellular phone, a laptop, a wearable remote device, a tablet (as shown in the embodiment of FIG. 1), or any other suitable mobile input device.

The local user interface 194 may be configured to display a graphical user interface. In embodiments where the remote caregiver interface 198 may also be configured to display a graphical user interface, the graphical user interface of the local user interface 194 may be identical to the graphical user interface of the remote caregiver interface 198. In other embodiments, the local caregiver interface 194 may replicate at least a portion of the graphical user interface of the remote user interface 198.

In some embodiments, the local user interface 194 may include a camera for capturing image data, referred to herein as the "user image data". For example, the user image data may be of the patient, a face of the patient, a person within a vicinity of the patient support apparatus 100, or the patient support apparatus 100 itself. Furthermore, the camera for capturing the user image data may be any suitable camera, such as a digital camera, a thermographic camera, a webcam, a video camera, a livestream broadcast camera, or any other device suitable for capturing the caregiver image data. Additionally, the camera for capturing the user image data may be disposed on or within the local user interface 194. Such features may allow the caregiver 196 to see the patient in the patient support apparatus 100 while the caregiver 196 controls the patient support apparatus 100.

In some embodiments, the local user interface 194 may include a microphone for capturing audio data, referred to herein as the "user audio data". For example, the audio data may be a voice of the patient or a voice of a person within the vicinity of the patient support apparatus 100. Furthermore, the microphone for capturing the user audio data may be any suitable microphone, such as a condenser microphone, a dynamic microphone, a piezoelectric microphone, an electret microphone, a wireless microphone, or a wearable microphone. Additionally, the microphone for capturing the caregiver audio data may be disposed on or within the local user interface 194. Such features may allow the caregiver 196 to hear the voice of the patient while the caregiver 196 controls the patient support apparatus 100.

Furthermore, it should be noted that, in various embodiments, the local user interface 194 may be defined differently. For example, in an embodiment where the local user interface 194 is disposed on the patient support apparatus 100, the local patient interface may be defined as being used by a person adjacent to or disposed on the patient support apparatus 100. However, in embodiments where the local user interface 194 is separated from the patient support apparatus 100, the local user interface 194 may be defined as being used by a person within the vicinity of the patient support apparatus 100. The person within the vicinity of the patient support apparatus 100 may be any one of the patient, a caregiver, a family member, a hospital staff member, or any other suitable person. However, in different embodiments, the vicinity of the patient support apparatus 100 may be defined differently. For example, in one embodiment, the local user interface 194 may be defined as being used by the patient disposed on the patient support apparatus 100. In another embodiment, the local user interface 194 may be defined as being used by a person within 50 feet of the patient support apparatus 100. In yet another embodiment, the local user interface 194 may be defined as being used by a person in the same room as the patient support apparatus 100.

The patient support apparatus 100 may also include a patient sensor 197. In FIG. 1, the sensing system 197 is illustrated as being disposed within the fourth side rail 174. However, in other embodiments, the patient sensor 197 may be disposed on or within the headboard 181, the footboard 182, any of the side rails 171, 172, 173, 174, the caregiver interfaces 183, or any other suitable component of the patient support apparatus 100.

The patient sensor 197 may include a variety of sensors for sensing a state of the patient. For example, the patient sensor 197 may include a heart rate sensor, a patient temperature sensor, a moisture sensor, a shear sensor, a neurological sensor, a load cell, a blood pressure sensor, a camera, a force sensor, a breathing monitor, a patient expression sensor, a patient acoustic sensor, a scale, a switch, an optical sensor, an infrared sensor, an electromagnetic sensor, an accelerometer, a potentiometer, an ultrasonic sensor, or combinations thereof for sensing the state of the patient.

As shown in FIG. 1, the controller 195, the remote caregiver interface 198, and the image sensor 193 may be coupled to a communication network 191 to communicate wirelessly with one another. The communication network 191 may be any suitable communication network. For example, the communication network 191 may include any one of Bluetooth, WiFi, Infrared, ZigBee, radio waves, cellular signals, any other suitable communication network, or combinations thereof. In some embodiments, the communication network 191 may include a networking device such as a gateway device, a router, or a repeater. In other embodiments, the controller 195, the remote caregiver interface 198, and the image sensor 193 may communicate with each other using peer-to-peer communication.

Figure 2:
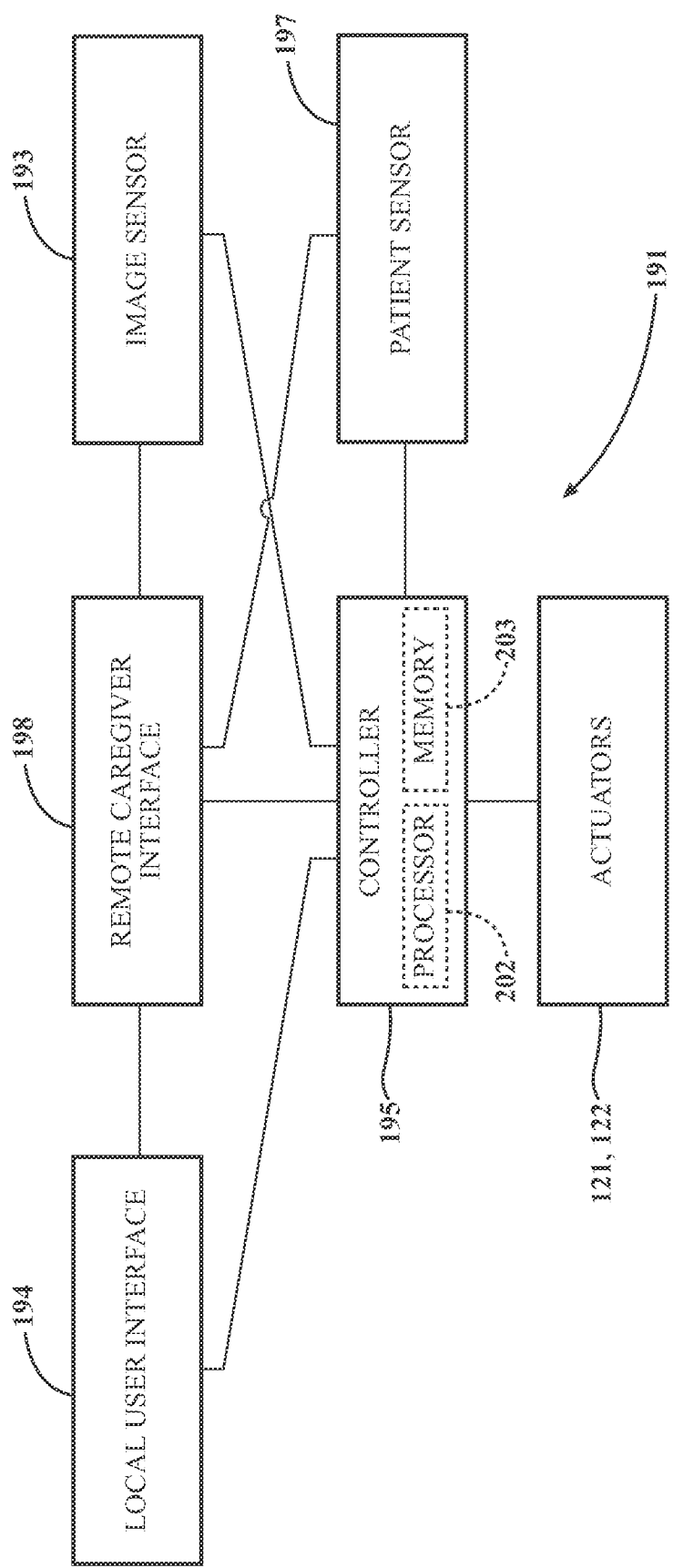
FIG. 2 is a schematic diagram illustrating the controller, the remote caregiver interface, and the image sensor.

FIG. 2 features a schematic diagram which further illustrates the communication network 191. In the embodiment shown in FIG. 2, the controller 195, the image sensor 193, the remote caregiver interface 198, the local user interface 194, and the patient sensor 197 may be coupled to one another via the communication network 191.

For example, as shown in FIG. 2, the controller 195 may be coupled to the remote caregiver interface 198 via the communication network 191 and may receive an input signal corresponding to a selected remote control function from the remote caregiver interface 198, referred to herein as the "remote input signal". The controller 195 may also be coupled to the local user interface 194 via the communication network 191 and may receive another input signal corresponding to a selected local control function from the local user interface 194, referred to herein as the "local input signal". Furthermore, the controller 195 is also coupled to the actuators 121, 122 of the patient support apparatus 100 and may transmit an output signal to the actuators 121, 122 to cause movement of the one or more actuatable devices 120 based on the remote input signal or the local input signal.

It should be noted that, in some embodiments, the controller 195 may be coupled to the local user interface 194 without using the communication network 191. For example, in an embodiment where the local user interface 198 is the user interface of the patient support apparatus 100, the local user interface 198 may be in direct communication with controller 195. As such, the controller 195 may receive the selected local control function without using the communication network 191.

As previously stated, the remote input signal corresponds to the selected remote control function from the remote caregiver interface 198. The selected remote control function may be categorized as a non-patient remote control function or a patient remote control function. A remote control function is categorized as a patient remote control function if the remote control function causes movement of the patient support apparatus 100, causes movement of one or more actuatable devices 120 that are configured to move a patient or contact a patient, or could result in a change of state of the patient support apparatus 100 that could have adverse consequences for the patient. For example, a patient remote control function may cause the actuator 121, 122 to lift the side rails 171, 172, 173, 174, apply a brake of the patient support apparatus 100, lift the patient support deck 140, or incline the back section (i.e., the head end) of the patient support deck 140. In contrast, a non-patient remote control function does not cause movement of the patient support apparatus 100. For example, a non-patient remote control function may cause the controller 195 to activate a speaker 185 of the patient support apparatus 100 to play music, activate one or more lights of the patient support apparatus 100, or activate other components of the patient support apparatus 100 which are unrelated to movement.

Also previously stated, the local input signal corresponds to the selected local control function from the local user interface 198. Similarly, the selected local control function may be categorized as a non-patient local control function or a patient local control function. More explicitly stated, a local control function may also be categorized as a patient local control function if the local control function causes movement of the patient support apparatus 100, causes movement of one or more actuatable devices 120 that are configured to move a patient or contact a patient, or could result in a change of state of the patient support apparatus 100 that could have adverse consequences for the patient.

In some embodiments, the selected local control function may override the selected remote control function. For example, in an embodiment where the controller 195 receives the remote input signal from the remote caregiver interface 198 and then receives the local input signal from the local user interface 194, the controller may abort the selected remote control function and execute the selected local control function. In an embodiment where the controller 195 receives the local input signal from the local user interface 194 and then receives the remote input signal from the remote caregiver interface 198, the remote control function may ignore the selected remote control function and execute the selected local control function. In another embodiment, the local input signal may cause the controller to abort the selected remote control function and return the patient support apparatus 100 to its initial state. Alternatively, the selected remote control function may override the selected local control function in a similar manner as described above.

In other embodiments, the selected local control function and the selected remote control function may both be executed. For example, in one embodiment, the controller 195 may execute both the selected remote control function and the selected local control function if no conflict exists. In an example embodiment, the selected local control function may cause the controller 195 to activate the speaker 185 to play music while the selected remote control function causes the actuators 121, 122 to lift the side rails 171, 172, 173, 174.

As shown in FIG. 2, the remote caregiver interface 198 and the controller 195 may be coupled to the image sensor 193 via the communication network 191 and may receive the patient support apparatus image data from the image sensor 193.

Also shown in FIG. 2, the remote caregiver interface 198 may be coupled to the local user interface 194 and may transmit the caregiver image data and the caregiver audio data to the local user interface 194 via the communication network 191. Similarly, the local user interface 194 may transmit the user image data and the user audio data to the remote caregiver interface 198.

In some embodiments, the controller 195 may be coupled to the image sensor 193 without using the communication network 191. For example, in an embodiment where the image sensor 193 is disposed within the patient support apparatus 100, the image sensor 193 and the controller 195 may be in direct communication with each other. As such, the controller 195 may receive the patient support apparatus image data without the use of the communication network 191.

Also shown in FIG. 2, the controller 195 and the remote caregiver interface 198 may be coupled to the patient sensor 197 via the communication network 191 and may receive a sensor input signal from the patient sensor 197. The patient sensor 197 may transmit the sensor input signal representing the state of the patient. For example, the sensor input signal may include a heart rate of the patient, a temperature of the patient, a moisture level of the patient support apparatus 100, a weight of the patient, a blood pressure of the patient, vital signs of the patient, and any other sensed parameter that may indicate the state of the patient.

In some embodiments, the controller 195 may be coupled to the patient sensor 197 without using the communication network 191. For example, in the embodiment shown in FIG. 1, the patient sensor 197 is disposed within the patient support apparatus 100. In such an embodiment, the patient sensor 197 and the controller 195 may be in direct communication with each other. As such, the controller 195 may receive the sensor input signal from the patient sensor 197 without the use of the communication network 191.

Additionally, as shown in FIG. 2, the controller 195 includes a memory 203 and a processor 202. The processor 202 may be any processor suitable for processing data. For example, the processor 202 may be a processor typically found in a desktop computer or a processor typically found in a mobile processing device such as a cellular phone, a tablet, or a laptop. Similarly, the memory 203 may be any memory suitable for storage of data and computer-readable instructions. For example, the memory 203 may be a local memory, an external memory, or a cloud-based memory embodied as random access memory (RAM), non-volatile RAM (NVRAM), flash memory, or any other suitable form of memory.

Figure 3A:
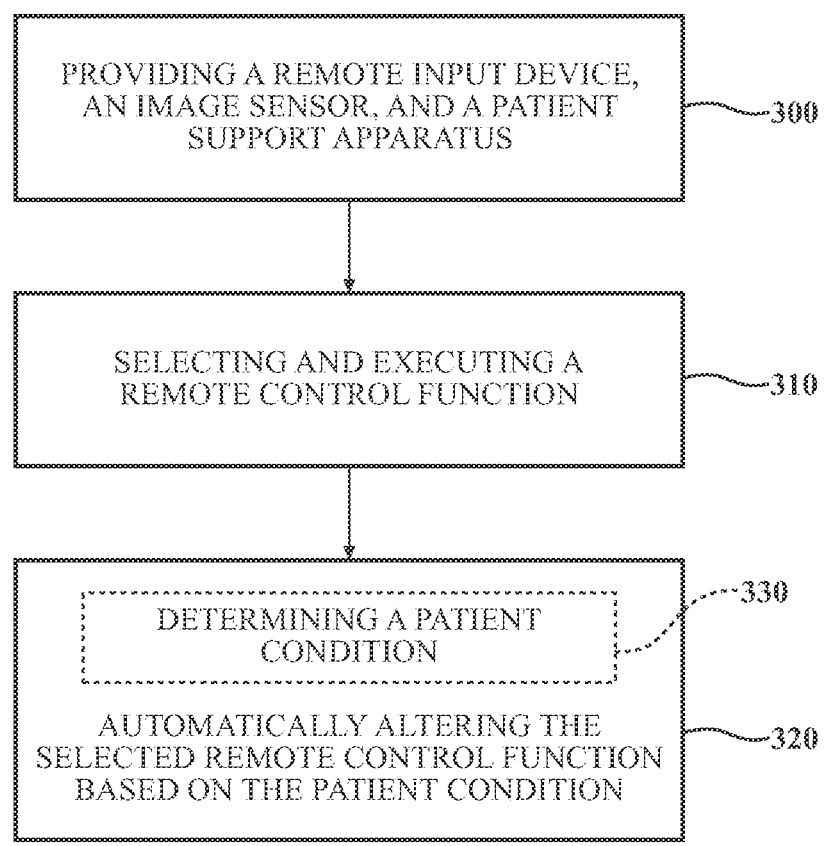
FIG. 3A is a flowchart illustrating a method for remotely controlling the patient support apparatus based on image data, which includes a step of selecting and executing a remote control function and a step of automatically altering the remote control function based on a patient condition.

To further aid in understanding the system 10, FIG. 3A provides a flowchart illustrating a method of remotely controlling the patient support apparatus 100 based on image data. As shown in FIG. 3A, the method may include a step 300 of providing the remote caregiver interface 198, the image sensor 193, and the patient support apparatus 100. The method may also include a step 310 of selecting and executing the remote control function and a step 320 of automatically altering the remote control function based on a patient condition. Also shown in FIG. 3A, step 320 may include a step 330 of determining the patient condition.

Figure 3B:
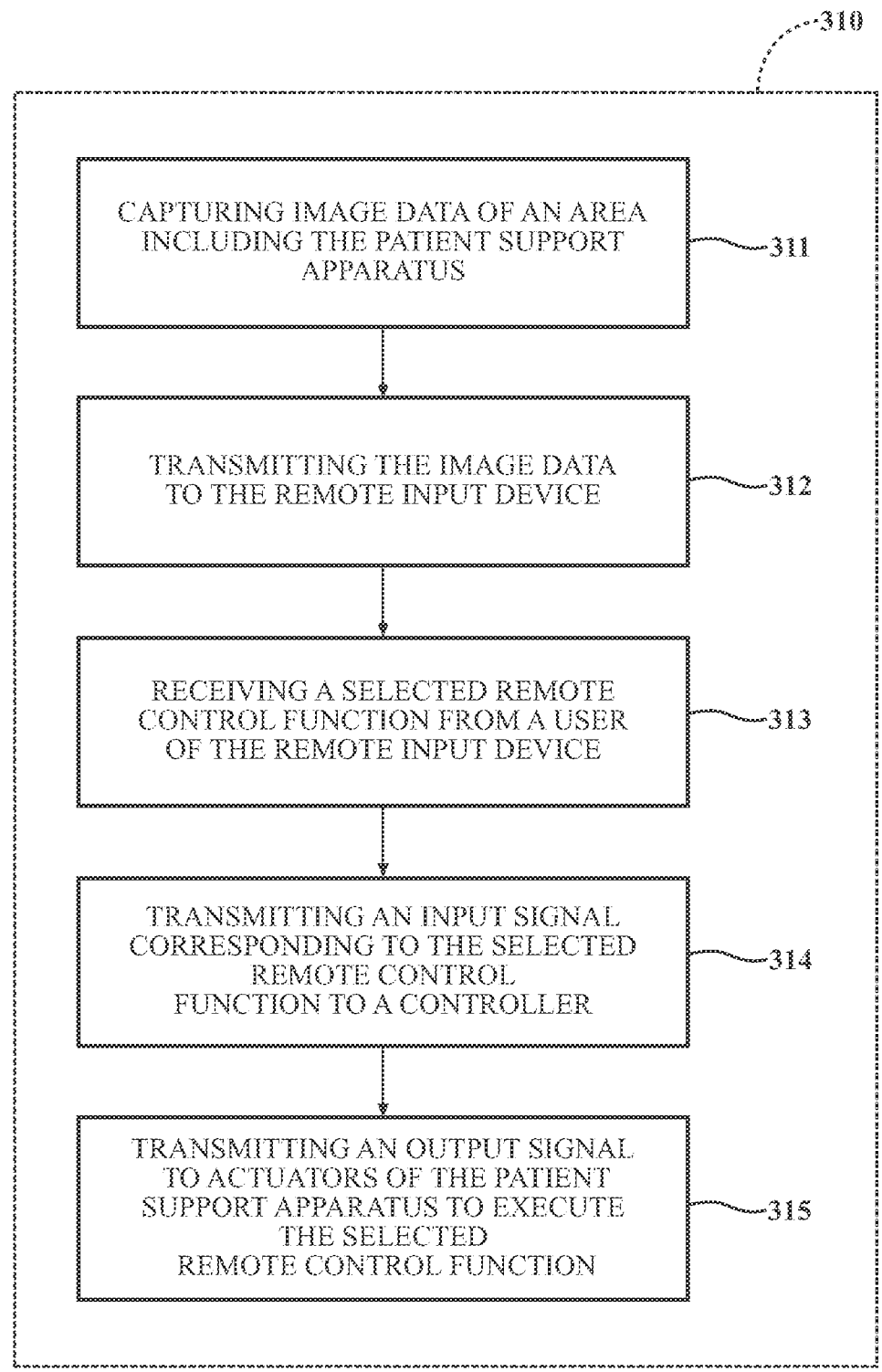
FIG. 3B is a flowchart illustrating the step of selecting and executing the remote control function.

Step 320 is further illustrated in FIG. 3B. As shown, the method may include a step 311 of capturing the patient support apparatus image data, a step 312 of transmitting the patient support apparatus image data to the remote caregiver interface 198, and a step 313 of receiving the selected remote control function from a user of the remote caregiver interface 198. In one embodiment, the image sensor 193 may perform steps 311 and 312 and the remote caregiver interface 198 may perform step 313. Additionally, it should be noted that the user of the remote caregiver interface 198, such as the caregiver 196, is able to view the patient support apparatus image data once it is transmitted and received by the remote caregiver interface 198. As such, the user of the remote caregiver interface 198 is able to select the remote control function based on the patient support apparatus image data. Of course, in some embodiments, the user of the remote caregiver interface 198 may select the remote control function without viewing the patient support apparatus image data or before the patient support apparatus image data is transmitted to or received by the remote caregiver interface 198.

An example embodiment may be used to further explain the method and may be referred to herein as the "foot section elevation embodiment". In the foot section elevation embodiment, the patient support apparatus image data captured during step 311 and transmitted during 312 may indicate that the patient is experiencing swelling in their legs. As a result, the caregiver 196 may use the remote caregiver interface 198 to select a remote control function during step 313 which, when executed, causes the actuators 121, 122 to elevate the foot section of the patient support deck 140, reducing the swelling in the patient's legs. This remote control function may be described herein as the "foot section elevation remote control function".

After receiving the selected remote control function during step 313, the method proceeds to a step 314 of transmitting the input signal corresponding to the remote control function, i.e. the remote input signal, to the controller 195 of the patient support apparatus 100. The method then continues to a step 315 of transmitting an output signal to the actuators 121, 122 of the patient support apparatus 100 to execute the remote control function. In one embodiment, the remote caregiver interface 198 may perform step 314 and the controller 195 may perform step 315. In the foot section elevation embodiment, the remote caregiver interface 198 transmits the input signal corresponding to the foot section elevation remote control function during step 314. Accordingly, the controller 195, during step 315, transmits the output signal to the actuators 121, 122 of the patient support apparatus 100, which elevates the foot section of the patient support deck 140.

Referring back to FIG. 3A, after the remote control function is selected and executed during step 310, the method may proceed to step 320 where the method determines the patient condition during step 330 and automatically alters the selected remote control function based on the patient condition. During step 320, the method may automatically alter the selected remote control function by automatically aborting the selected remote control function, modifying the selected remote control function, or selecting a new remote control function. Furthermore, the method may automatically alter the selected remote control function while the selected remote control function is being executed. For example, in the foot section elevation embodiment, the method may abort the foot section elevation remote control function during step 320 and cease elevation of the foot section of the patient support deck 140. As another example, the method may modify the foot section elevation remote control function during step 320 by elevating the foot section of the patient support deck 140 at a slower speed. As yet another example, the method may select a different remote control function during step 320 by causing the actuators 121, 122 to incline the back section of the patient support deck 140 instead of elevating the foot section of the patient support deck 140.

The method may also automatically alter a patient therapy protocol during step 320. In some embodiments, the remote control function may be further defined as a patient therapy protocol. As previously discussed, the remote control function may be categorized as a non-patient remote control function or a patient remote control function. The patient remote control function may be further categorized as a discrete patient remote control function or a periodic patient remote control function. As used herein, a discrete patient remote control function causes the controller 195 to execute a singular command. For example, a discrete patient remote control function may cause the actuators 121, 122 to lift the patient support deck 140 or incline the back section of the patient support deck 140 a single instance. As used herein, a periodic patient remote control function causes the controller 195 to execute a singular command periodically. For example, a periodic patient remote control function may cause the actuators 121, 122 to elevate a foot section of the patient support deck 140 every hour. The patient therapy protocol is an example of a periodic patient remote control function. The patient therapy protocol may be defined as including a set of desired therapeutic actions which cause movement of one or more actuatable devices 120 to provide therapy to the patient and may be periodically executed during "instances" of the patient therapy protocol. For example, in one embodiment of the patient therapy protocol, the patient therapy protocol may cause the actuators 121, 122 to turn the patient every half hour to reduce a risk of acquiring pressure ulcers. As used herein, this embodiment of the patient therapy protocol may be referred to as the "patient turning embodiment" and the corresponding patient therapy protocol may be referred to as the "patient turning therapy protocol".

In an embodiment where the selected remote control function is a patient therapy protocol, the method may automatically alter the patient therapy protocol at any time during the patient therapy protocol. More explicitly stated, the method may automatically abort, modify, or select a different remote control function before, during, or after any instance of the patient therapy protocol. For example, in the patient turning embodiment, the method may abort the patient turning therapy protocol during step 320 and cease turning the patient. As another example, the method may modify the patient turning therapy protocol during step 320 by turning the patient at a faster speed. As yet another example, the method may select a different remote control function during step 320 by causing the actuators 121, 122 to elevate the foot section of the patient support deck 140 every hour or by causing the actuators 121, 122 to incline the back section of the patient support deck. Furthermore, in the patient turning embodiment, the method may automatically alter the patient therapy protocol before the actuators 121, 122 turn the patient, while the actuators 121, 122 are turning the patient, and after the actuators 121, 122 turn the patient.

Figure 3C:
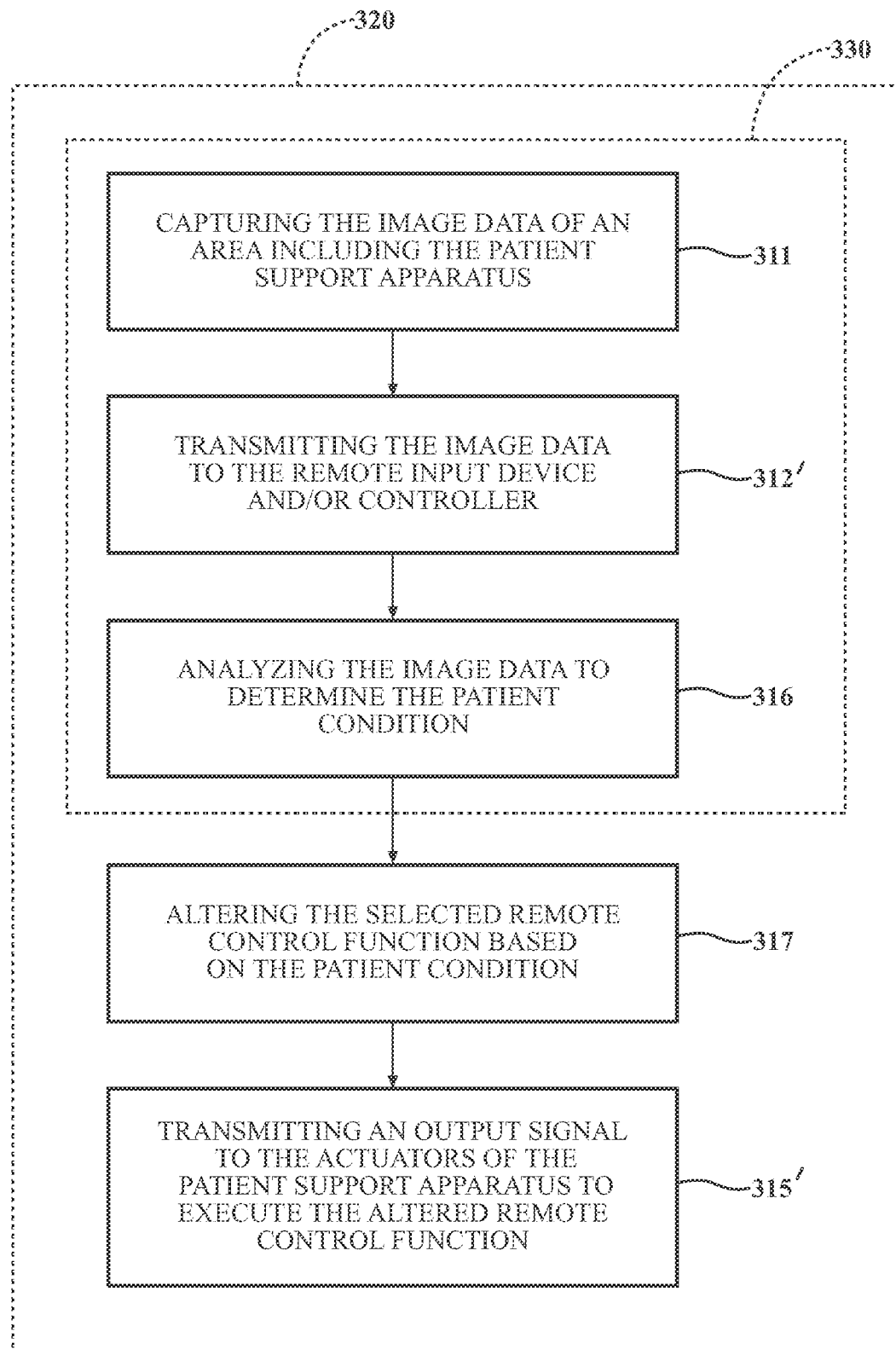
FIG. 3C is a flowchart illustrating the step of automatically altering the remote control function based on the patient condition.

Step 320 is further shown in FIG. 3C. As previously discussed, step 320 includes the step 330 of determining the patient condition. As shown, step 330 includes the step 311 of capturing the patient support apparatus image data. Step 330 may also include a step 312'. Step 312' is similar to step 312 because, during both steps, the method transmits the patient support apparatus image data to the remote caregiver interface 198. However, during step 312', the method may also transmit the patient support apparatus image data to the controller 195. In one embodiment, the image sensor 193 may perform steps 311 and 312'.

As shown in FIG. 3C, step 330 may also include the step 316 of analyzing the patient support apparatus image data to determine the patient condition. The patient condition may include a patient presence, a comfort indication of the patient, a physiological state of the patient, or combinations thereof. For example, in the patient turning embodiment, the remote caregiver interface 198 and/or the controller 195 may analyze the patient support apparatus image data and determine that the patient is suffering from nausea. In another example, the remote caregiver interface 198 and/or the controller 195 may analyze the thermal patient support apparatus image data and determine that the patient has a fever.

As previously stated, the patient support apparatus image data is sent to the remote caregiver interface 198 and/or the controller 195 during step 312'. As such, the remote caregiver interface 198 and/or the controller 195 may perform step 316. In other words, the remote caregiver interface 198 and/or the controller 195 may analyze the patient support apparatus image data to determine the patient conditions.

Additionally, it should be noted that the remote caregiver interface 198 and the controller 195 may use any suitable image analysis technique to determine the patient condition. For instance, the remote caregiver interface 198 and the controller 195 may use edge detection techniques, object recognition techniques, motion detection techniques, and video tracking techniques to analyze the patient support apparatus image data and determine the patient condition.

After step 316, the method proceeds to a step 317 of automatically altering the selected remote control function based on the patient condition. As previously described, the method may automatically alter the selected remote control function by aborting the selected remote control function, modifying the selected remote control function, or selecting a new remote control function. For example, in the patient turning embodiment, the remote caregiver interface 198 and/or the controller 195 determines that the patient is suffering from nausea during step 316. As follows, the remote caregiver interface 198 and/or the controller 195 may automatically alter the selected remote control function during step 317 by modifying the patient turning therapy protocol to turn the patient at a slower rate.

Furthermore, it should be noted that the selected remote control function may be altered based on the patient condition, which may be determined by the remote caregiver interface 198 and/or the controller 195 during step 330. As such, the remote caregiver interface 198 and/or the controller 195 may perform step 317. However, in some embodiments, if the remote caregiver interface 198 alters the selected remote control function during step 330, the remote caregiver interface 198 may also transmit another input signal to the controller 195 corresponding to the altered remote control function, referred to herein as the "altered input signal".

After the method alters the selected remote control function based on the patient condition, the method proceeds to a step 315' of transmitting the output signal to the actuators 121, 122 to execute the altered remote control function. Step 315' is similar to step 315, except step 315' transmits the output signal to execute the altered remote control function instead of the selected remote control function. Just as the controller 195 may perform step 315, the controller 195 may also perform step 315'.

Additionally, it should be noted that, during step 315', the output signal may vary depending on how the selected remote control function is altered during step 317. For example, in the patient turning embodiment, the method may modify the patient turning therapy protocol during step 317 to turn the patient at the slower rate. As such, the controller 195 transmits the output signal to the actuators 121, 122, causing the actuators 121, 122 to turn the patient at the slower rate during step 315'. In an embodiment where the selected remote control function is aborted during step 317, the controller 195 may cease transmission of the output signal during step 315'. In an embodiment where a new remote control function is selected during step 317, the controller 195 may transmit the output signal to the actuators 121, 122 to execute the new remote control function during step 315'.

Figure 4:
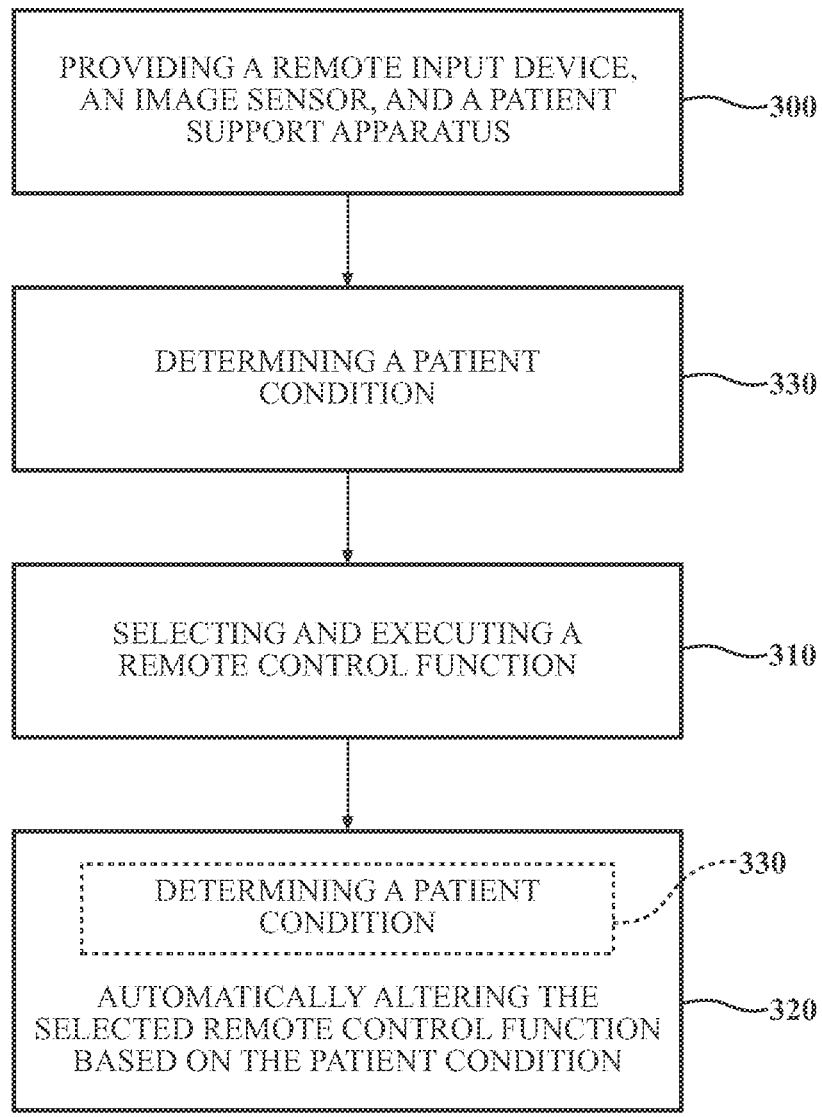
FIG. 4 is a flowchart illustrating a second embodiment of the method, which includes a step of determining the patient condition before the step of selecting and executing the remote control function.

FIG. 4 is a flowchart illustrating an embodiment of the method where the method determines the patient condition during step 330 before selecting and executing the remote control function during step 310. In such an embodiment, the patient condition may trigger step 310. For example, in the patient turning embodiment, after the method determines that the patient has a high risk of acquiring a pressure ulcer during step 330, the method proceeds to step 310, where the patient support apparatus image data is captured and transmitted to the remote caregiver interface 198 for viewing by the caregiver 196. The caregiver 196 may then select the appropriate remote control function, such as the patient turning therapy protocol, to reduce the patient's risk of acquiring a pressure ulcer.

In another embodiment, the patient condition may be presented to the user of the remote caregiver interface 198 before step 310. As such, the user of the remote caregiver interface 198 may view the patient condition before selecting and executing the remote control function during step 313. For example, in the foot section elevation embodiment, the method may determine that the patient is experiencing swelling in their legs and present this patient condition to the caregiver 196. The caregiver 196 may then view the patient condition and the patient support apparatus image data before selecting the foot section elevation remote control function to reduce the swelling in the patient's leg. Of course, in some embodiments, the patient condition may be presented to the user of the remote caregiver interface 198 after step 312 of step 310, but before 313. In such embodiments, the patient condition may be presented to the caregiver 196 after the patient support apparatus image data is transmitted to the remote caregiver interface 198, but before the caregiver 196 selects the remote control function. Furthermore, the method may also notify the caregiver 196 of the patient condition after the method determines the patient condition. The method may notify the caregiver 196 using a tactile, audio, or visual alert on the remote caregiver interface 198.

Figure 5A:
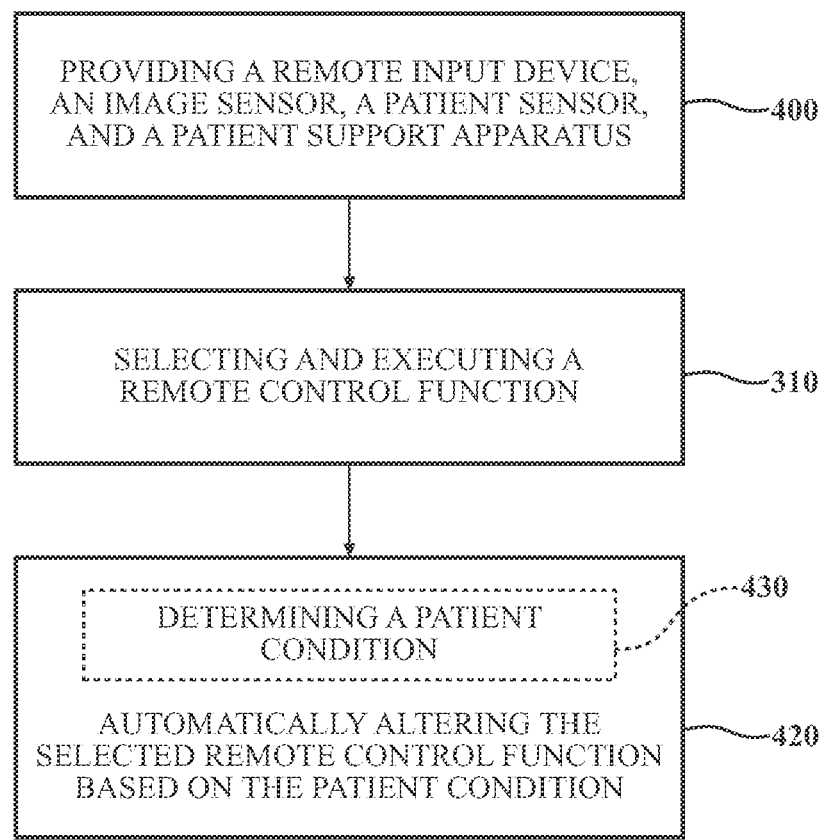
FIG. 5A is a flowchart illustrating a third embodiment of the method, which includes a step of providing a patient sensor, the step of selecting and executing the remote control function, and a step of automatically altering the remote control function based on the patient condition.
Figure 5B:
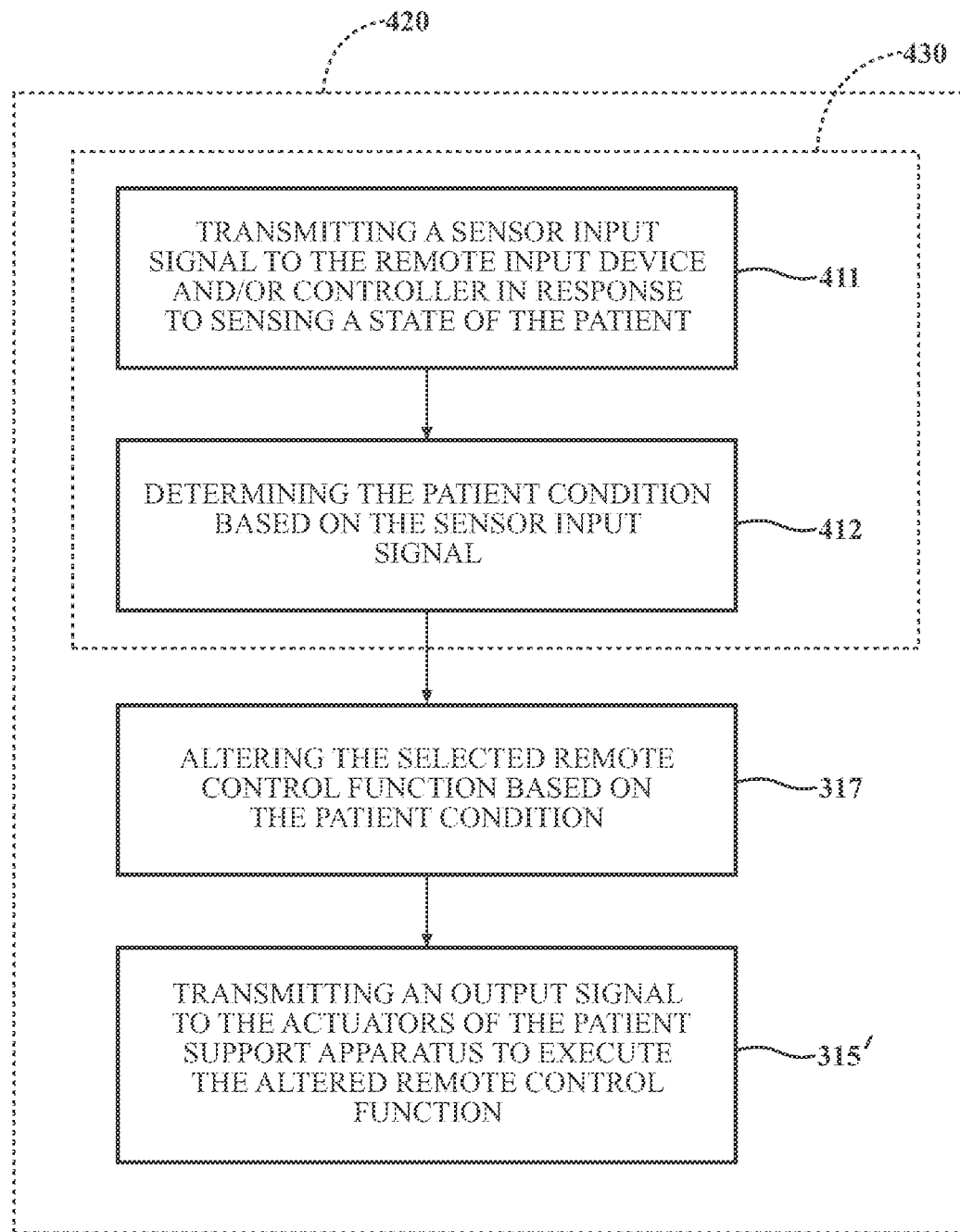
FIG. 5B is a flowchart illustrating the step of automatically altering the remote control function based on the patient condition of the third embodiment of the method.

As previously discussed, the system 10 may include the patient sensor 197. FIG. 5A provides a flowchart illustrating an embodiment of the method where the system 10 includes the patient sensor 197. As shown, the method may include a step 400 of providing the remote caregiver interface 198, the image sensor 193, the patient sensor 197, and the patient support apparatus 100. The method may also include the previously described step 310 of selecting and executing the remote control function and a step 420 of automatically altering the selected remote control function based on the patient condition. As shown, step 420 may include a step 430 of determining the patient condition.

It should be noted that step 420 and step 430 of FIG. 5A are similar to step 320 and 330 of FIG. 3A. In both step 420 and step 320, the method may automatically alter the selected remote control function by automatically aborting the selected remote control function, modifying the selected remote control function, or selecting a new remote control function. Similarly, in both step 430 and step 330, the method determines the patient condition. However, because the method in FIG. 5A provides the patient sensor 197 during step 400, there are some differences between steps 420 and 430 and steps 320 and 330.

For example, while the method of FIG. 3A may perform steps 311, 312', and 316 to determine the patient condition during step 330, the method of FIG. 5A may perform steps 411 and 412 to determine the patient condition during step 430. During step 411, the method transmits the sensor input signal to the remote caregiver interface 198 and/or the controller 195 in response to sensing the state of the patient. During step 412, the method determines the patient condition based on the sensor input signal. In one embodiment, the patient sensor 197 may perform step 411. Furthermore, because the sensor input signal input signal is transmitted to the remote caregiver interface 198 and/or the controller 195, the remote caregiver interface 198 and/or the controller 195 may determine the patient condition during step 412. In one embodiment, the remote caregiver interface 198 and/or the controller 195 may determine the patient condition by comparing the sensor input signal to a threshold value or by performing a calculation based on the sensor input signal. For example, the sensor input signal may provide a measurement of the patient's systolic and diastolic blood pressure. The remote caregiver interface 198 and/or the controller 195 may determine that the patient's condition is hypertensive if the systolic and diastolic blood pressures exceed predetermined thresholds (e.g., 140 mm Hg and 90 mm Hg, respectively). After the method determines the patient condition during step 330, the method may proceed to the previously described step 317 and step 315'.

Figure 6:
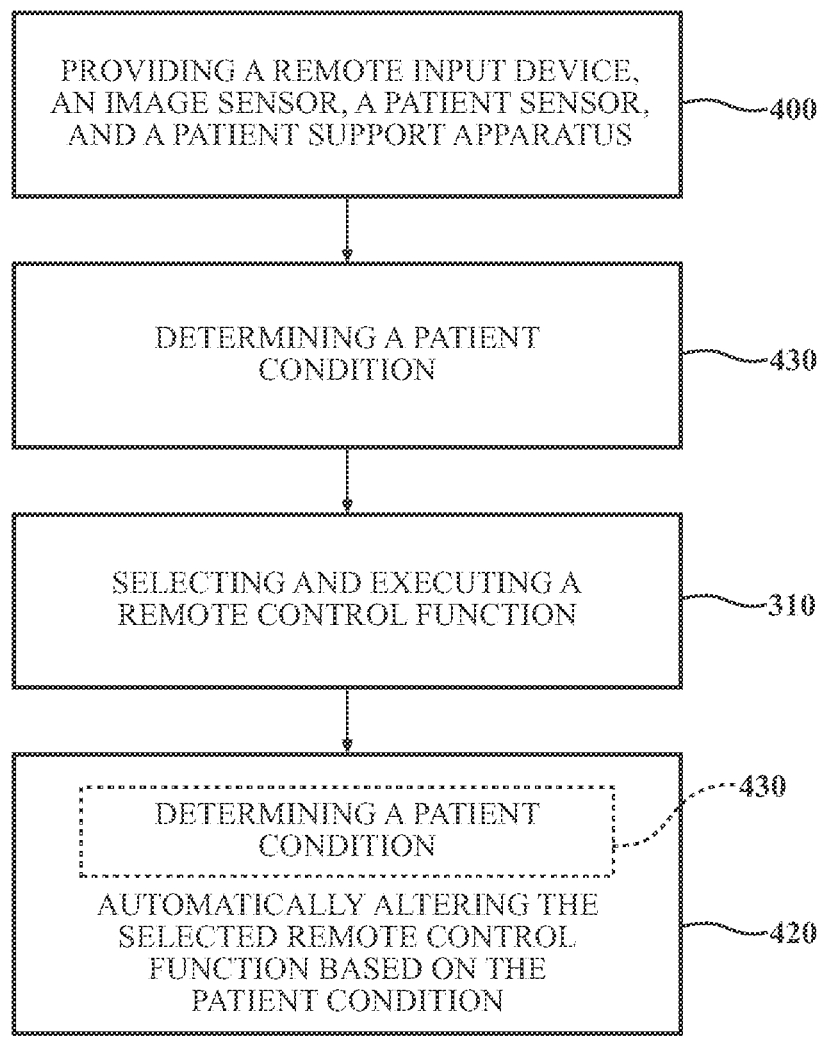
FIG. 6 is a flowchart illustrating a fourth embodiment of the method, which includes the step of determining the patient condition before the step of selecting and executing the remote control function.

FIG. 6 provides a flowchart illustrating an embodiment of the method where the method determines the patient condition during step 430 before selecting and executing the remote control function during step 310. Similar to the embodiment shown in FIG. 4 where step 330 triggers step 310 step, here in FIG. 6, step 430 may trigger step 310. Furthermore, the patient condition may be presented to the user of the remote caregiver interface 198 after the patient condition is determined during step 430. The patient condition may be presented to the user of the remote caregiver interface 198 before step 310 or after step 312 of step 310, but before step 313 of step 310. Furthermore, the method may also notify the caregiver 196 of the patient condition using a tactile, audio, or visual alert on the remote caregiver interface 198 after the method determines the patient condition.

Figure 7:
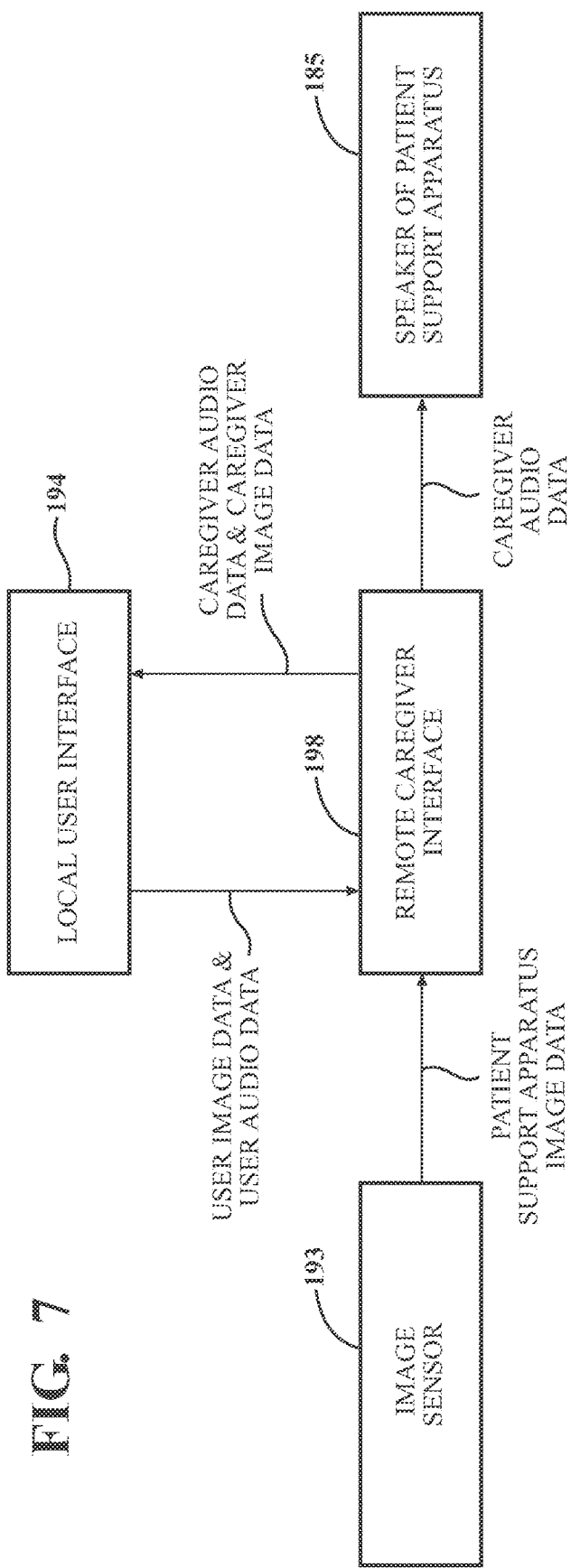
FIG. 7 is a schematic diagram illustrating the remote caregiver interface, a local user interface, the image sensor, and a speaker of the patient support apparatus.

FIG. 7 is a schematic diagram illustrating the remote caregiver interface 198, the local user interface 194, the image sensor 193, and the speaker 185 of the patient support apparatus 100. As previously discussed, and shown in FIG. 7, the remote caregiver interface 198 may receive the user image data and the user audio data from the local user interface 194. Furthermore, the remote caregiver interface 198 may receive the patient support apparatus image data from the image sensor 193. Additionally, the remote caregiver interface 198 may capture the caregiver audio data and the caregiver image data. As shown, the remote caregiver interface 198 may transmit the caregiver audio data and the caregiver image data to the local user interface 194. The remote caregiver interface 198 may also transmit the caregiver audio data to the speaker 185.

As such, in some embodiments, the remote caregiver interface 198 may receive the user image data and the user audio data from the local user interface 194 and transmit the caregiver audio data to the speaker 185. Similarly, the remote caregiver interface 198 may receive the patient support apparatus image data from the image sensor 193 and transmit the caregiver audio data to the speaker 185. In another embodiment, the remote caregiver interface 198 may receive the user image data and the user audio data from the local user interface 194 and transmit the caregiver audio data and the caregiver image data to the local user interface 194. In such an embodiment, the caregiver 196 may see a face of the patient and hear a voice of the patient via the remote caregiver interface 198 and the patient may see a face of the caregiver 196 and hear a voice of the caregiver 196 via the local user interface 194. As such, the caregiver 196 and the patient may initiate a video conference with each other.

Furthermore, the remote caregiver interface 198 may transmit the caregiver audio data to the local user interface 194 or the speaker 185 without the caregiver image data. In this way, the caregiver 196 may speak to the patient via the local user interface 194 or the speaker 185 without sending an image of himself or herself to the patient. The remote caregiver interface 198 may also transmit the caregiver image data to the local user interface 194 without the caregiver audio data. In this way, the caregiver 196 may send an image of himself or herself to the patient via the local user interface 194 without speaking to the patient. Similarly, the local user interface 194 may only transmit the user image data to the remote user interface 198 without the user audio data or only transmit the user audio data to the remote caregiver interface 198 without the user image data. In each of these embodiments, a "partial communication" is executed.

Additionally, it should be appreciated that the remote caregiver interface 198 may transmit the caregiver audio data and/or the caregiver image data without receiving the user image data, the user audio data, and/or the patient support apparatus image data. Similarly, the remote caregiver interface 198 may receive the user image data, the user audio data, and/or the patient support apparatus image data without transmitting the caregiver audio data and/or the caregiver image data. As follows, the local user interface 194 may receive the caregiver audio data and/or the caregiver image data without transmitting the user image data and/or the user audio data. For example, the remote caregiver interface 198 may transmit the caregiver audio data to the local user interface 194 to provide the patient or another caregiver within a vicinity of the patient support apparatus 100 with a command from the caregiver 196. The local user interface 194 may also transmit the user image data and/or the user audio data without receiving the caregiver audio data and/or the caregiver image data. For example, the local user interface 194 may transmit the user audio data to the remote caregiver such that the patient may communicate with the caregiver 196 to provide the caregiver 196 with a request from the patient. In each of these embodiments, a "one-way communication" is executed.

It should be noted that, at any point during the above described methods, the remote caregiver interface 198 may begin receiving the user image data, the user audio data, and/or the patient support apparatus image data. Furthermore, at any point during the above described methods, the remote caregiver interface 198 may transmit the caregiver audio data and/or the caregiver image data. As such, the caregiver 196 may, at any time during the method, view the patient, the face of the patient, a person within a vicinity of the patient support apparatus 100, or the patient support apparatus 100 itself, and/or hear the voice of the patient or the voice of a person within the vicinity of the patient support apparatus 100. Similarly, the patient may, at any time during the method, view the caregiver 196, the face of the caregiver 196, and/or hear the voice of the caregiver 196. As such, the caregiver 196 and the patient may communicate with one another at any time, allowing the caregiver 196 to better understand the patient's symptoms, to select an appropriate remote control function, to warn a patient of an imminent remote control function, or to speak with the patient during execution of the remote control function.

Figure 8:
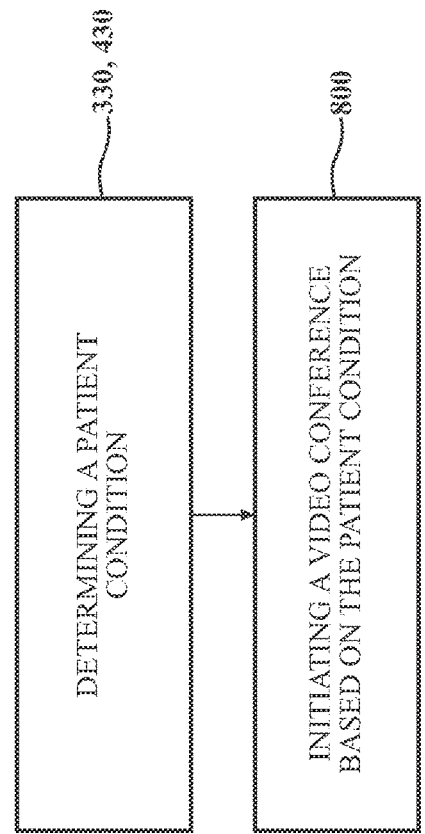
FIG. 8 is a flowchart illustrating a method of initiating a video conference based on the patient condition.

FIG. 8 provides a flowchart illustrating a method of initiating the video conference based on the patient condition. As shown, the method may include step 330 or step 430 to determine the patient condition. Accordingly, the method may determine the patient condition by analyzing the patient support apparatus image data from the image sensor 193 during step 330 or by analyzing the sensor input signal from the patient sensor 197 during step 430. After determining the patient condition, the method proceeds to a step 800 of initiating the video conference between the local user interface 194 and the remote caregiver interface 198 based on the patient condition.

It should be noted that, during step 330, the patient support apparatus image data may be transmitted to the remote caregiver interface 198 and/or the controller 195. Similarly, during step 430, the sensor input signal may be transmitted to the remote caregiver interface 198 and/or the controller 195. As such, after the remote caregiver interface 198 and/or the controller 195 may determine the patient condition, the remote caregiver interface 198 and/or the controller 195 may initiate the video conference based on the patient condition. More explicitly stated, during step 800, the controller 195 or the remote caregiver interface 198 may initiate the video conference between the local user interface 194 and the remote caregiver interface 198.

As previously described, after determining the patient condition during step 330 or step 430, the method may initiate the video conference between the local user interface 194 and the remote caregiver interface 198 based on the patient condition during step 800. In some embodiments, the method may automatically initiate the video conference after determining the patient condition. In further embodiments, the method may automatically initiate the video conference a period of time after determining the patient condition. For example, if the method determines that the patient is experiencing cardiac arrest, the method may automatically initiate the video conference between the local user interface 194 and the remote caregiver interface 198. In another example, if the method determines that the patient is experiencing nausea, the method may automatically initiate the video conference 5 minutes after the determination if the patient is still experiencing nausea.

In another embodiment, the method may determine the patient condition during step 330 or step 430 and transmit a signal representative of the patient condition to the caregiver 196 via the remote caregiver interface 198. In such an embodiment, the caregiver 196 may optionally initiate the video conference between the local user interface 194 and the remote caregiver interface 198. For example, if the method determines that the patient is suffering from dehydration, the method may allow the caregiver 196 to initiate the video conference between the local user interface 194 and the remote caregiver interface 198. The caregiver 196 may advise the patient to drink water.

In other embodiments, the method may automatically end the video conference after determining the patient condition. In further embodiments, the method may automatically end the video conference a period of time after determining the patient condition. In still further embodiments, the method may also transmit the signal representative of the patient condition to the caregiver 196 via the remote caregiver interface 198 and allow the caregiver 196 to end the video conference. For example, after the method determines that the patient has returned to a stable state, the method may automatically end the video conference, automatically end the video conference after 1 minute, or allow the caregiver 196 to end the video conference.

It should be noted that the method may automatically initiate or end the video conference, initiate or end the video conference after a period of time, or allow the caregiver to initiate or end the video conference based on the patient condition. For example, if the patient condition is an emergency patient condition, such as cardiac arrest, or an allergic reaction, the method may automatically initiate the video conference. In another example, if the patient condition is lower risk patient condition, such as discomfort or a fever, the video conference may allow the caregiver to initiate the video conference based on the patient condition. Similarly, if the patient condition is an emergency patient condition, the method may allow the caregiver to end the video conference even after the patient has returned to a stable state. If the patient condition is a lower risk patient condition, the method may automatically end the video conference after the patient has returned to a stable state.

Furthermore, the method may execute a partial communication or a one-way communication, as defined above, based on the patient condition. For example, if the patient is suffering from dehydration, the method may execute a one-way communication by activating the speaker 185, allowing the caregiver to instruct the patient to drink water. In another example, if the patient is experiencing a sensitivity to light, the method may execute a partial communication where the local user interface 194 only receives the caregiver audio data and the screen of the local user interface 194 is not illuminated.

In the previously described methods, the methods may, at any time, receive the local control function from the local user interface 194. As previously stated, the local control function may override the selected remote control function. In such an embodiment, the local control function may, at any time, abort the selected remote control function or select a local control function to replace the selected remote control function.

Furthermore, in the previously described methods, the methods may perform a step indefinitely. For example, the method may continuously capture the patient support apparatus image data during step 311. As another example, the method may continuously transmit the patient support apparatus image data during step 312 and step 312' and continuously transmit the sensor input signal during step 411. As yet another example, the method may continuously determine the patient condition during step 316 and step 412.

FIG. 9 illustrates an example embodiment of the remote caregiver interface 198 and a graphical user interface 901 of the remote caregiver interface 198. In FIG. 9, the remote caregiver interface 198 is a cellular phone, which may be used by a caregiver 196. As shown, the graphical user interface 901 may provide a variety of remote control functions 902 for selection by the caregiver 196. Furthermore, the remote caregiver interface 198 may provide measurements 904 of the patient support apparatus 100, such as a height of the patient support apparatus 100 or an incline of the patient support apparatus 100. Additionally, the graphical user interface may provide the patient support apparatus image data or a graphical representation 904 of the patient support apparatus 100, which may update to reflect changes in the patient support apparatus 100.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

The invention claimed is:

1. A system for remotely controlling a medical device based on image data, the system comprising:
a medical device comprising a patient support apparatus including:
a controller coupled to a communication network,
a support structure with a patient support surface to support a patient, and
an actuatable device coupled to the patient support apparatus and operable to facilitate treatment of the patient
an image sensor coupled to the communication network and being configured to capture image data and to transmit the image data to the controller; and
a remote caregiver interface coupled to the communication network and configured to:
display the image data for viewing by a user of the remote caregiver interface,
receive a selected remote control function from the user corresponding to operation of the actuatable device, and
transmit an input signal corresponding to the selected remote control function to the controller of the medical device;
wherein the controller is configured to:
analyze the image data to determine a patient condition;
alter the selected remote control function based on the patient condition; and
transmit an output signal to the actuatable device to execute the altered remote control function to facilitate treatment of the patient.

2. The system as set forth in claim 1, wherein the patient condition comprises a patient presence, a comfort indication of the patient, a physiological state of the patient, or combinations thereof.

3. The system as set forth in claim 1, wherein the remote caregiver interface is further configured to:
analyze the image data from the image sensor to determine a patient condition;
alter the selected remote control function based on the patient condition; and
transmit an input signal corresponding to the altered remote control function to the controller; and
wherein the controller is further configured to:
transmit an output signal to the actuatable device to execute the altered remote control function based on the input signal corresponding to the altered remote control function.

4. The system as set forth in claim 1, further comprising a patient sensor configured to transmit a sensor input signal in response to sensing a state of the patient;
wherein the controller is further configured to receive the sensor input signal and determine the patient condition based on the sensor input signal; and
wherein the controller is further configured to:
alter the remote control function based on the patient condition, and
transmit an output signal to the actuatable device to execute the altered remote control function.

5. The system as set forth in claim 4, wherein the patient sensor is coupled to the communication network and wherein the remote caregiver interface is further configured to receive the sensor input signal and determine the patient condition based on the sensor input signal;
wherein the remote caregiver interface is further configured to:
alter the remote control function based on the patient condition, and
transmit an input signal corresponding to the altered remote control function based on the patient condition; and
wherein the controller is further configured to transmit the output signal to the actuatable device to execute the altered remote control function based on the input signal corresponding to the altered remote control function.

6. The system as set forth in claim 1, wherein the image sensor comprises an infrared image sensor, a visual light image sensor, or a combination thereof.

7. The system as set forth in claim 1, wherein the communication network is a wireless network.

8. The system as set forth in claim 1, further comprising a local user interface configured to transmit a selected local control function to the controller.

9. The system as set forth in claim 8, wherein the local user interface is configured to display a graphical user interface; and
wherein the remote caregiver interface is configured to display a graphical user interface, the graphical user interface on the remote caregiver interface being identical to the graphical user interface on the local user interface.

10. The system as set forth in claim 8, wherein the local user interface is configured to display a graphical user interface; and
wherein the remote caregiver interface is further configured to replicate at least a portion of the graphical user interface displayed on the local user interface.

11. The system as set forth in claim 1, wherein the image sensor is coupled to the patient support apparatus.

12. The system as set forth in claim 1, wherein image sensor is coupled to a support structure near the patient support apparatus.

13. The system as set forth in claim 1, wherein the remote caregiver interface is a mobile device.

14. The system as set forth in claim 1, wherein the remote caregiver interface comprises a camera, the camera configured to capture image data of the user of the remote caregiver interface.

15. The system as set forth in claim 14, further comprising a local user interface coupled to the communication network and being proximate to the patient support apparatus, the local user interface being configured to receive the image data of the user from the remote caregiver interface.

16. The system as set forth in claim 15, wherein the remote caregiver interface is further configured to initiate a video conference with the local user interface and wherein the local user interface is further configured to initiate the video conference with the remote caregiver interface.

17. The system as set forth in claim 15, wherein one of the controller and the remote caregiver interface is further configured to:
determine a patient condition; and
initiate a video conference with the local user interface based on the patient condition.

18. The system as set forth in claim 1, wherein the actuatable device comprises a lighting device, a temperature device, a humidity device, or combinations thereof.

19. The system as set forth in claim 1, wherein the actuatable device comprises a vibrational therapy device, a percussion therapy device, compression therapy device, a patient warming device, an electrical stimulation device, or combinations thereof.

* * * * *